United States Patent [19]
Heiberger et al.

[11] Patent Number: 5,356,593
[45] Date of Patent: Oct. 18, 1994

[54] APPARATUS FOR MEASUREMENT OF BLOOD SATURATION AND HEMATOCRIT

[75] Inventors: Robert A. Heiberger, Boulder; Jon S. Ingebrigtsen, Lakewood; James R. Price, Westminster, all of Colo.

[73] Assignee: Cobe Laboratories, Inc., Lakewood, Colo.

[21] Appl. No.: 943,281

[22] Filed: Sep. 10, 1992

Related U.S. Application Data

[63] Continuation of Ser. No. 656,804, Feb. 15, 1991, abandoned.

[51] Int. Cl.⁵ .................... A61M 1/14; A61B 5/00; G01N 21/84
[52] U.S. Cl. .................... 422/45; 422/82.05; 422/82.11; 385/56; 128/634
[58] Field of Search ............ 422/45, 82.05; 385/56, 385/58, 59, 45, 88, 89, 92, 71; 606/15, 16; 604/905; 128/634, 666, 667; 607/92, 93

[56] References Cited

U.S. PATENT DOCUMENTS

| | | | |
|---|---|---|---|
| 4,243,883 | 1/1981 | Schwarzmann | 250/343 |
| 4,411,491 | 10/1983 | Larkin et al. | 350/96.21 |
| 4,423,923 | 1/1984 | Frazier et al. | 350/96.15 |
| 4,722,337 | 2/1988 | Losch et al. | 606/16 |
| 4,754,328 | 6/1988 | Barath et al. | 358/98 |
| 4,925,268 | 5/1990 | Iyer et al. | 350/96.29 |
| 4,943,182 | 7/1990 | Hoblingre | 403/349 |
| 5,007,704 | 4/1991 | McCartney | 385/56 |
| 5,073,042 | 12/1991 | Mulholland et al. | 385/69 |

FOREIGN PATENT DOCUMENTS 0361999  4/1990  European Pat. Off. .
2648918 12/1990  France .

Primary Examiner—Robert J. Warden
Assistant Examiner—E. Leigh Dawson

[57] ABSTRACT

Medical equipment for use in for example measurement of hematocrit and oxygen saturation in blood in which a connector portion includes protuberances to draw the portion relatively toward a probe, a window to cooperate with the probe, and a ramp and slot to cooperate with the probe to selectively limit its rotation.

28 Claims, 11 Drawing Sheets

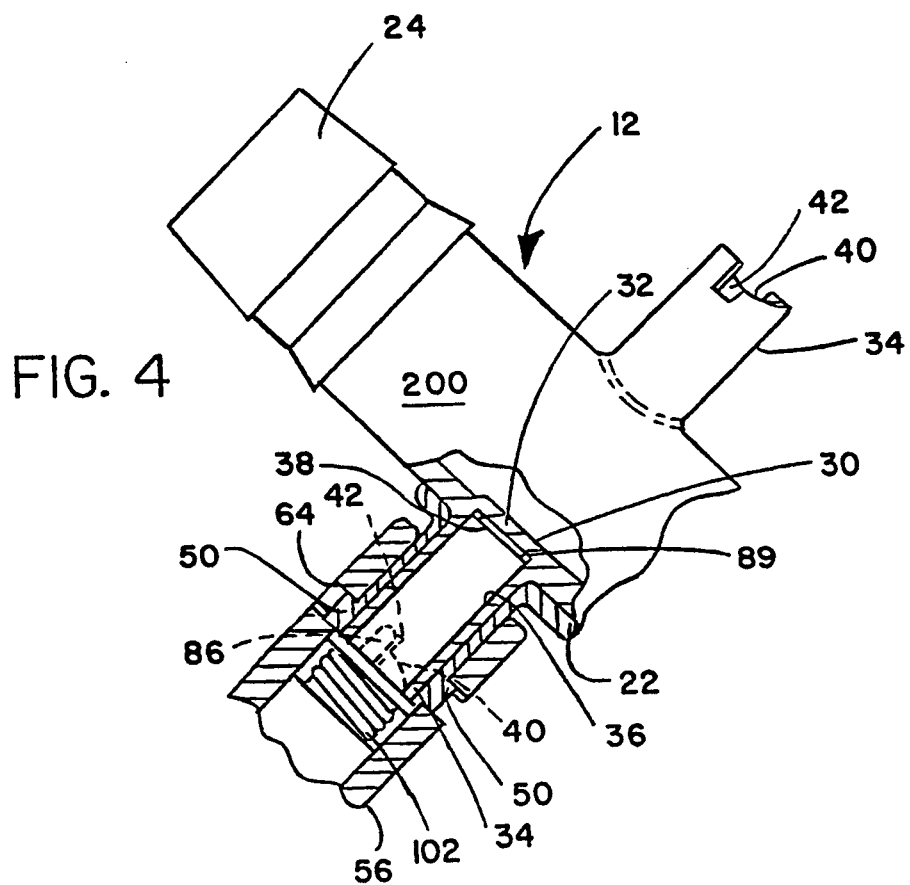
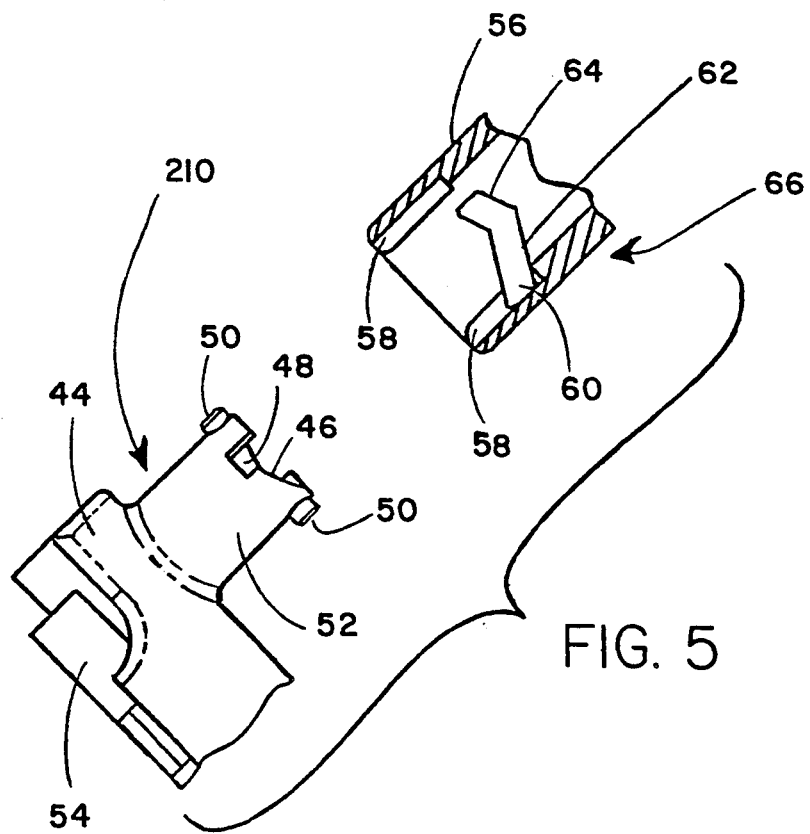

APPARATUS FOR MEASUREMENT OF BLOOD SATURATION AND HEMATOCRIT

This application is a continuation of application Ser. No. 656,804, filed Feb. 15, 1991, now abandoned.

FIELD OF THE INVENTION

The invention relates to measurement of blood saturation and hematocrit.

BACKGROUND OF THE INVENTION

It is known to measure hematocrit and saturation of blood by passing red light and infrared light through blood in shorter and longer paths, and using the differences in light energy remaining to calculate hematocrit and saturation.

Fused glass fiber optic connectors in a general Y configuration are known in the art.

SUMMARY OF THE INVENTION

It has been discovered that a receptor for accepting a probe for measurement of hematocrit and saturation desirably includes a blind probe hole the bottom of which is a blood window, means to drive the probe tip against the window, and means to prevent relative rotation in tip-window contact.

In preferred embodiments, protuberances cooperate with mating tube portions to drive probe toward and away from receptor, and ramps and a groove prevent the relative rotation mentioned.

In preferred embodiments a single fiber source of both infrared and red light is used, optical light sources being pulsed alternately through a fiber optic element with three legs, two source legs from respectively red and infrared light sources merging into a single optical leg.

PREFERRED EMBODIMENT

There is shown in the drawings, and described in the following specification, the structure of the presently preferred embodiment of the invention, and its operation.

DRAWINGS

The preferred embodiment is shown in the following drawings.

FIG. 4 is a side elevation view of said venous inlet, partially broken away and partially in section, in conjunction with the probe of the invention, shown broken away and in section.

FIG. 5 is an exploded view of portions of said venous inlet and (in vertical sectional view) said probe.

STRUCTURE

Figure 1:
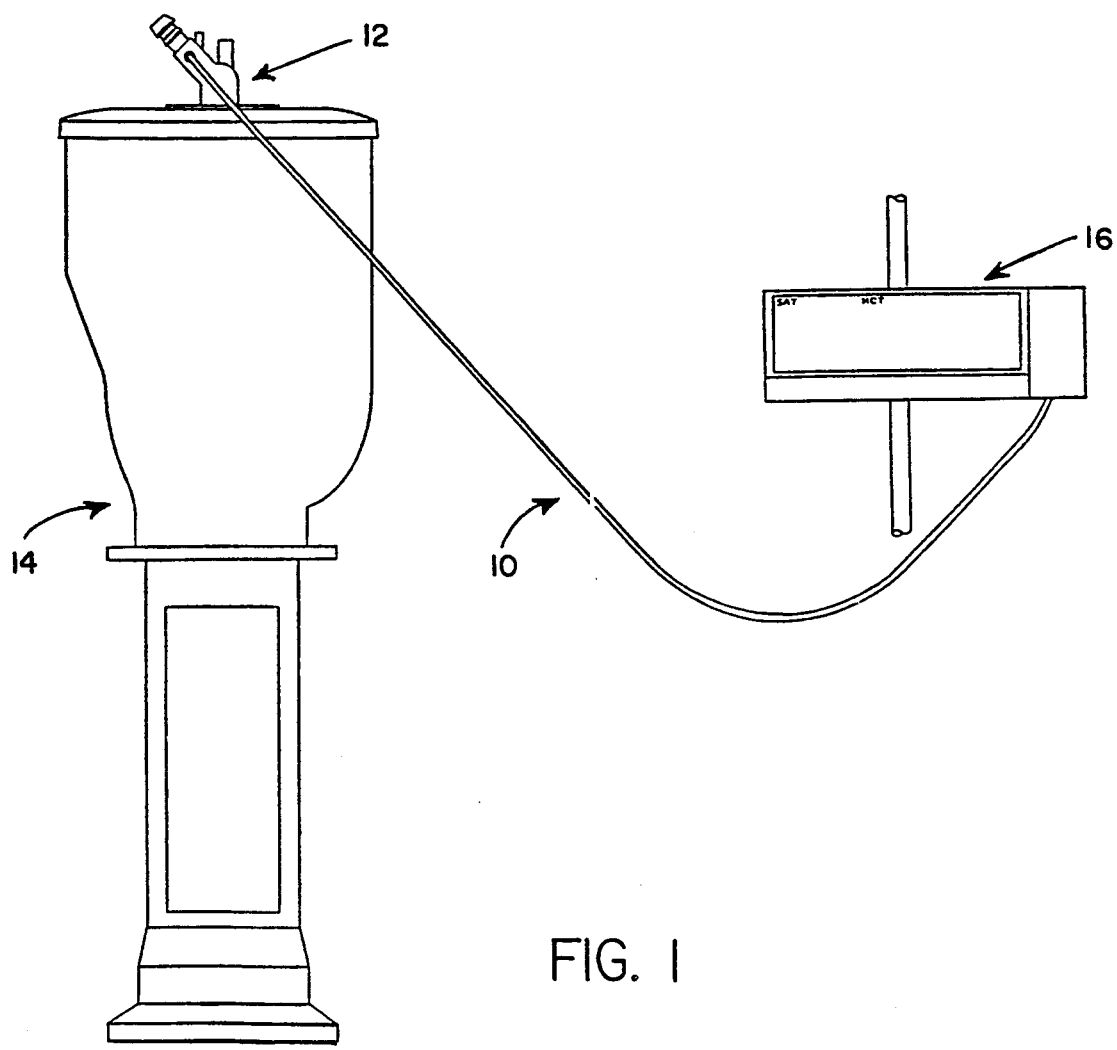
FIG. 1 is a somewhat diagrammatic side elevational view of the preferred embodiment including an oxygenator.

There is shown in FIG. 1, indicated at 10, a novel subassembly for a probe 66 of the invention, connected into venous inlet 12 of oxygenator 14 and control box 16.

Figure 2:
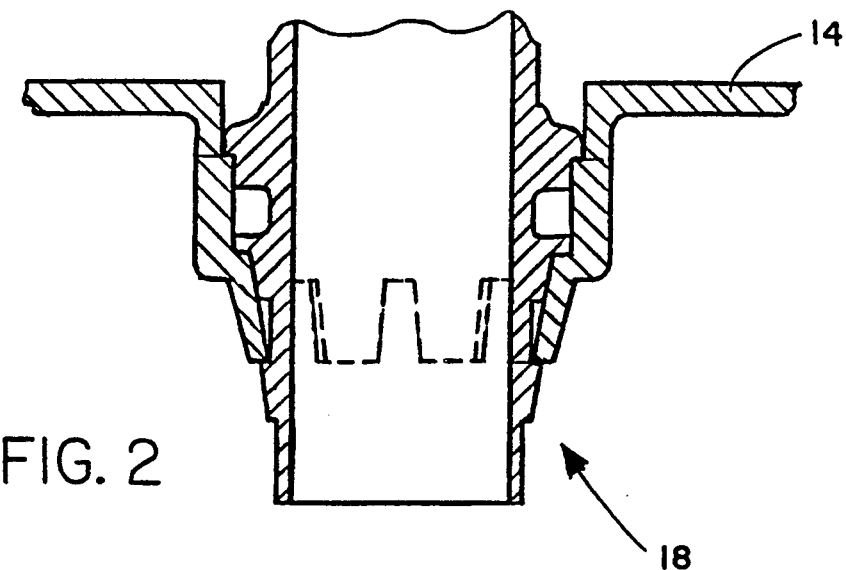
FIG. 2 is a vertical sectional view of the venous inlet portion of said preferred embodiment.

In FIG. 2 is shown lower portion 18 of venous inlet 12, which is latchably interfitted with the upper portion, as shown, of oxygenator 14.

Figure 3:
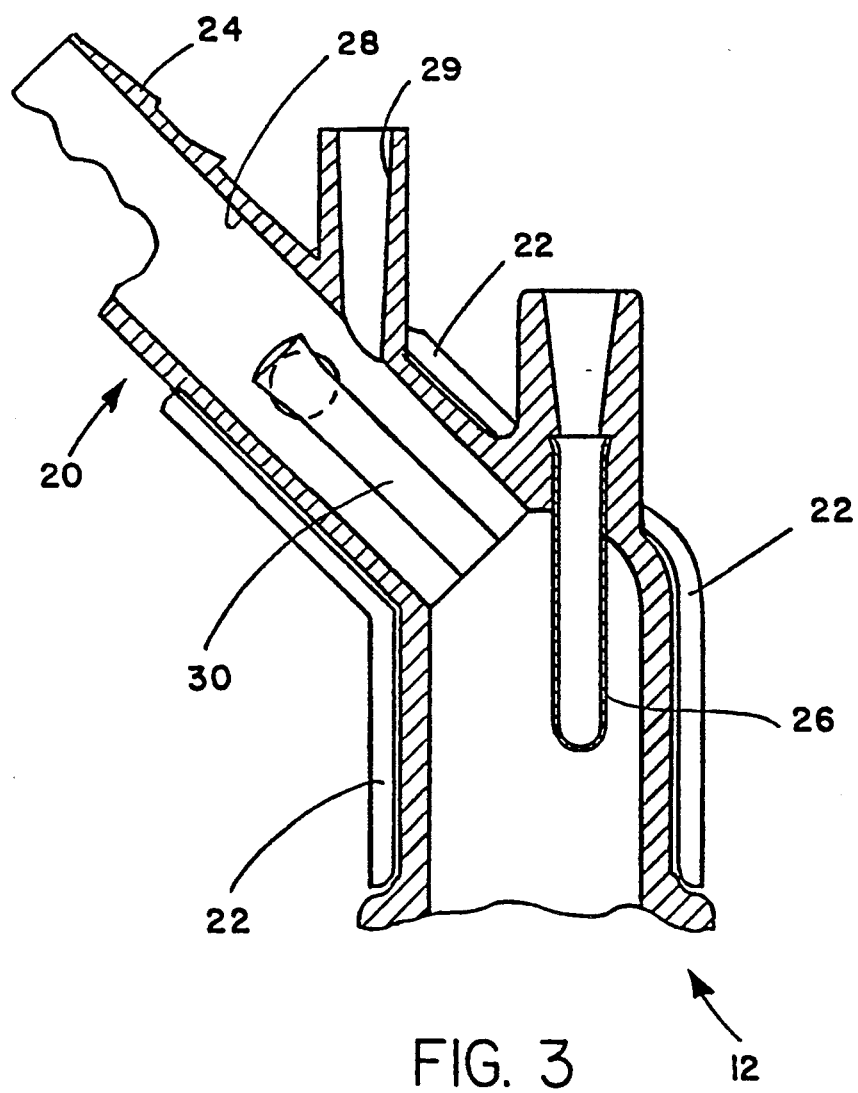
FIG. 3 is a vertical sectional view of said venous inlet in its upper portion, showing one of its surrounding shrouds.
Figure 6:
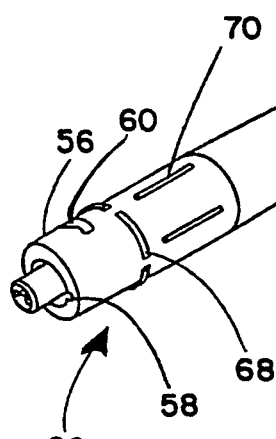
FIG. 6 is a broken-away view of a portion of said probe.
Figure 7:
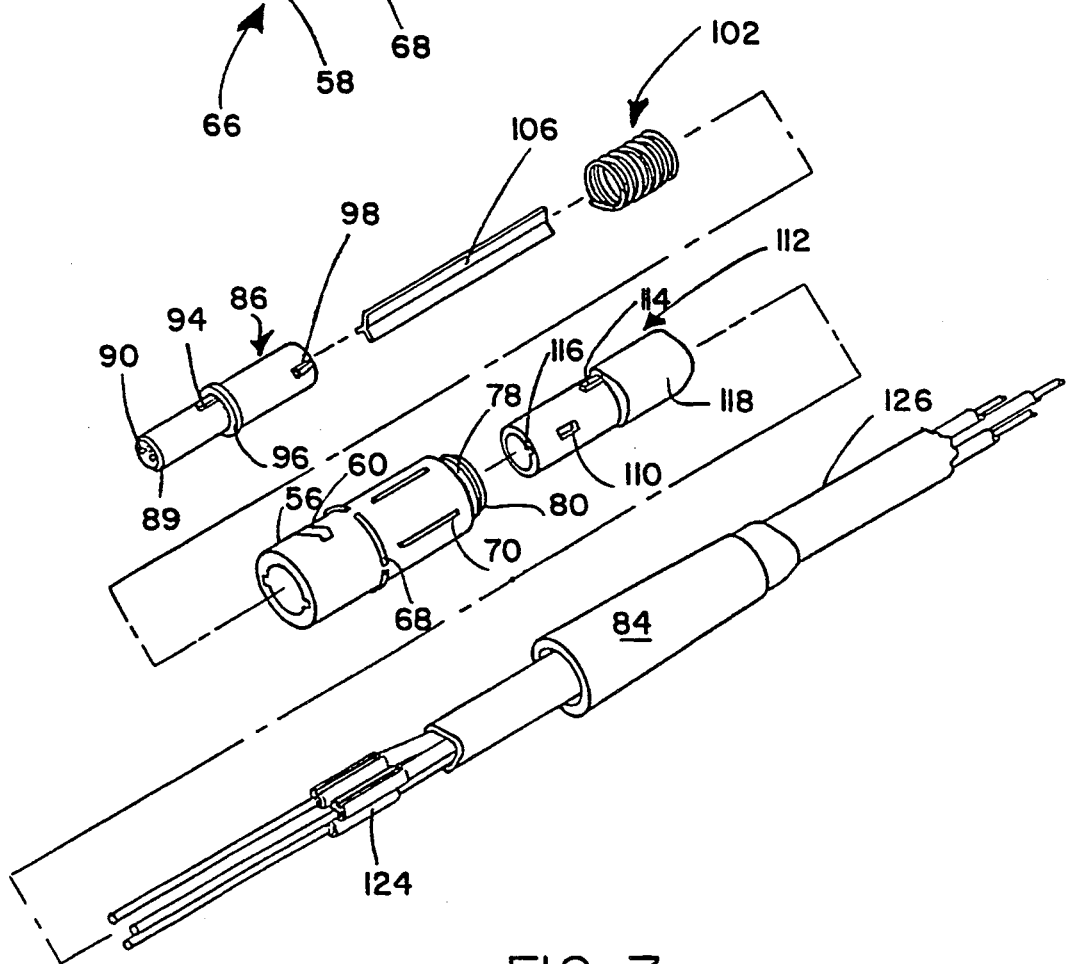
FIG. 7 is an exploded view of the portion of FIG. 6.
Figure 8:
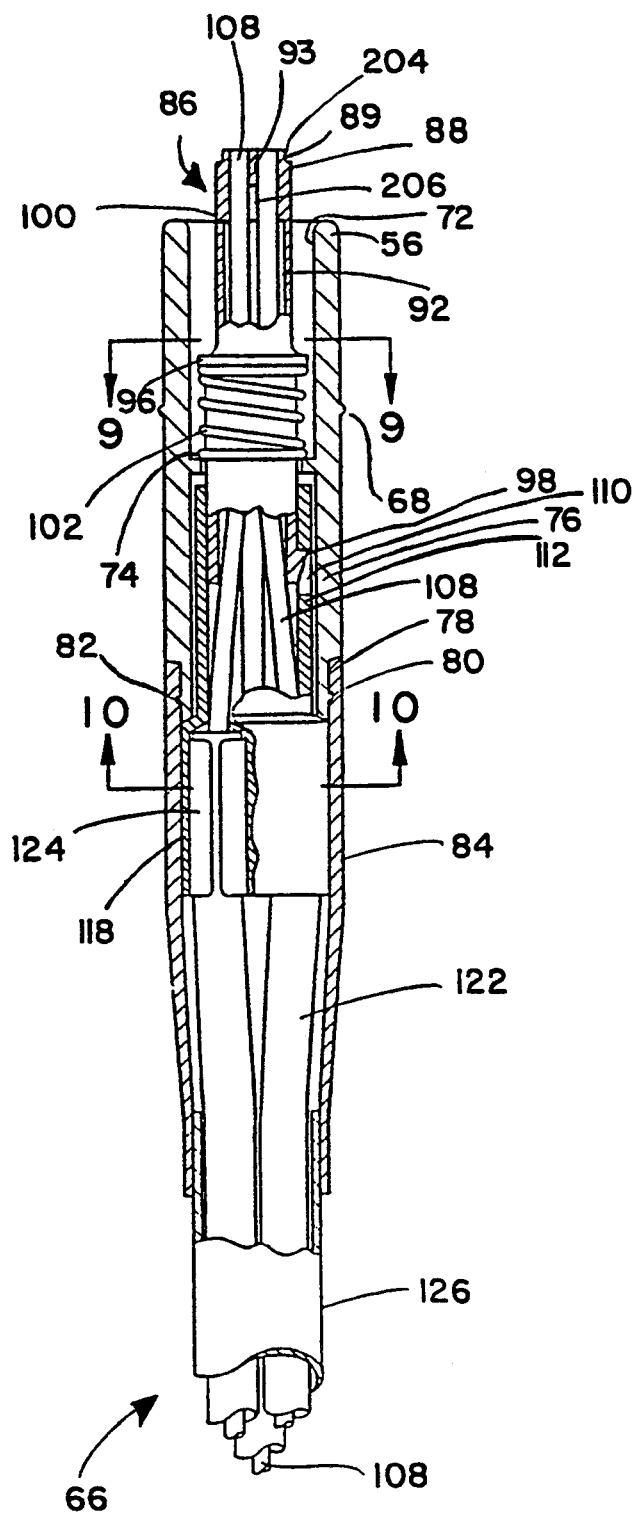
FIG. 8 is a sectional view of the portion of FIG. 6.

In FIG. 3 is shown upper portion 20 of venous inlet 12, surrounded over about half its periphery by plastic shroud portion 22. Inlet 12 includes an upper barb portion 24 for connection with tubing (not shown) for connection to a vein of a patient, and a molded-in metal thermometer well 26. Extending along inner bore 28 are flats 30, circumferentially spaced 180°. Also included is arterial sample line return (and drug administration) port 29, which is connected by a line (not shown) to an arterial blood sampling connection (not shown) downstream of oxygenator 14.

In FIG. 4 is shown a further view of the venous inlet 12, taken from a point of view 90° from that of FIG. 3. Flats 30 (of which there are two, located 180° apart) define the inner surfaces of windows 32 (circumferentially spaced 180°), which are formed of transparent polycarbonate plastic. Protruding integrally as portions of venous inlet 12 are probe receiving portions 34 which include each a blind hole 36 terminating in surfaces 38 defining the inner faces of windows 32, 0.035 inches thick. Each portion 34 terminates in a pair of (spaced 180° and correspondingly ramped) cam surfaces 40 and a pair of notches 42.

Portions 34 and most of the rest of inlet 12 are surrounded by shroud members 22 and 44 (the latter not shown in FIG. 4, but being of plastic, like member 22, and being latchedly connected therewith in position around inlet 12).

There is shown in FIG. 5 the other shroud portion 44, which, like shroud portion 22, includes two cam or ramp portions 46 circumferentially spaced 180°, and two notches 48, also circumferentially spaced 180°.

There are also shown in FIG. 5 two ears 50, circumferentially spaced 180° around portion 52, each ear extending circumferentially outwardly a short distance from portion 52. Shroud member 22 carries in the same way a pair of ears 50.

Shroud portion 44 is shown (diagrammatically) with latch portion 54, which engages latch portions on shroud portion 22 to secure portions 22 and 44 together in circumferential embrace of venous inlet 12.

Shroud portions 52 fit loosely around inlet portions 34, with ramp portions 46 extending alongside ramp portions 40 in essentially common helices, and notches 48 and 42 being correspondingly sized and axially and circumferentially positioned.

Shown in FIG. 5 placed for cooperative engagement with shroud portion 52 is probe collar 56, which has a generally tubular configuration the end inside periphery of which is interrupted by a pair of longitudinally extending grooves 58 of width to just accept ears 50, and of length to enable said ears to reach camming slots (one on each side, circumferentially spaced 180°, one for each ear 50) 60 which have a first ramping portion 62 extending from related groove 58 at an angle to the collar 56 axis of 60° for a first circumferential length of 90°, and a second ramping portion 64 then at an angle to the axis of 75° for a second circumferential distance of 15°.

If desired, the torque required to remove the probe end may be increased by shortening the distance between the ears 50 and a surface against which probe collar 56 abuts, as by adding shoulders to shroud 44 at the base of portion 52. This causes bending of ears 50, imposing a spring force resisting untwisting which supplements the force imposed by spring 102.

The probe 66 is shown in FIGS. 6 through 10.

Probe collar 56 includes slightly protruding circumferential projections 68 and longitudinal projections 70. Internally of collar 56 are provided counterbore 72 (FIG. 8), with spring support ledge 74, and counterbore 76. The end of collar 56 away from optical windows 32 includes circumferential groove 78 and ridge 80, the latter snapped into circumferential groove 82 of elastomeric boot 84.

Extending through collar 56 is probe tip 86 which includes end portion 88 with reduced diameter extremity 89 through which extend four holes 90. Abutting portion 88 is blind hole 92, which extends to the end 204 of probe tip 86. The walls 93 between holes 90 extend only about half way from the extremity of tip 86 to blind hole 92. Tip 86 also includes longitudinally extending alignment key 94, circumferential ledge 96, and axially extending male latching portion 98.

Held in compression between collar ledge 74 and tip ledge 96 is spring 102.

Extending from bottom 100 of blind hole 92 to beyond tip 86 in grooves 104 is plastic divider Y 106.

Extending through three of the holes 90 and through the three zones defined with blind hole 92 by divider 106 are three optical fibers 108; these are step index optical fibers with a polymethyl-methacrylate core and transparent "fluorine polymer" cladding, sold by AMP Corporation of Harrisburg, Pa., under the designation "ESKA Extra EH 4001", 1000 microns in diameter.

Epoxy potting material introduced through the remaining hole 90 fills that hole, the zones 206, and the spaces between blind hole 92, Y 106, and the fibers in the latter, down vertically (in FIG. 8) almost to ledge 96.

Fiber separator 106 separates fibers 108, reducing undesirable cross-talk among them, as well as in manufacture guiding fibers 108 to the correct holes 100. Gaps 206 in the walls between holes 90 allow bending of fibers 108 as necessary to thread them from separator 106 through holes 100, and facilitate potting.

Latchedly secured to tip 86 through latch 98 in hole 110 therein is plastic body 112, which carries longitudinally extending key 114 which fits in a depression (not shown) in the inner diameter surface of probe collar 56. Slot 116 enables latch 98 to ride therein until it reaches hole 110. Latch 98 is ramped and rides up into window 110, into which it snaps to lock together the entire assembly. Body 112 includes larger portion 118 through which extend three holes 120. Through holes 120 extend insulated (insulation not separately shown in FIG. 10) fiber optic portions 122, held in body 112 by barbed (with small directional barbs resisting movement in a disassembly direction only) grommets 124. Gaps or zones 206 improve moldability and even out wall thickness.

Sheath 126 is frictionally secured in boot 84 and extends around insulated fibers 122.

The other end of probe 66 is identical with the end already described, fibers 108 extending thus from one end of the probe to the other.

Figure 12:
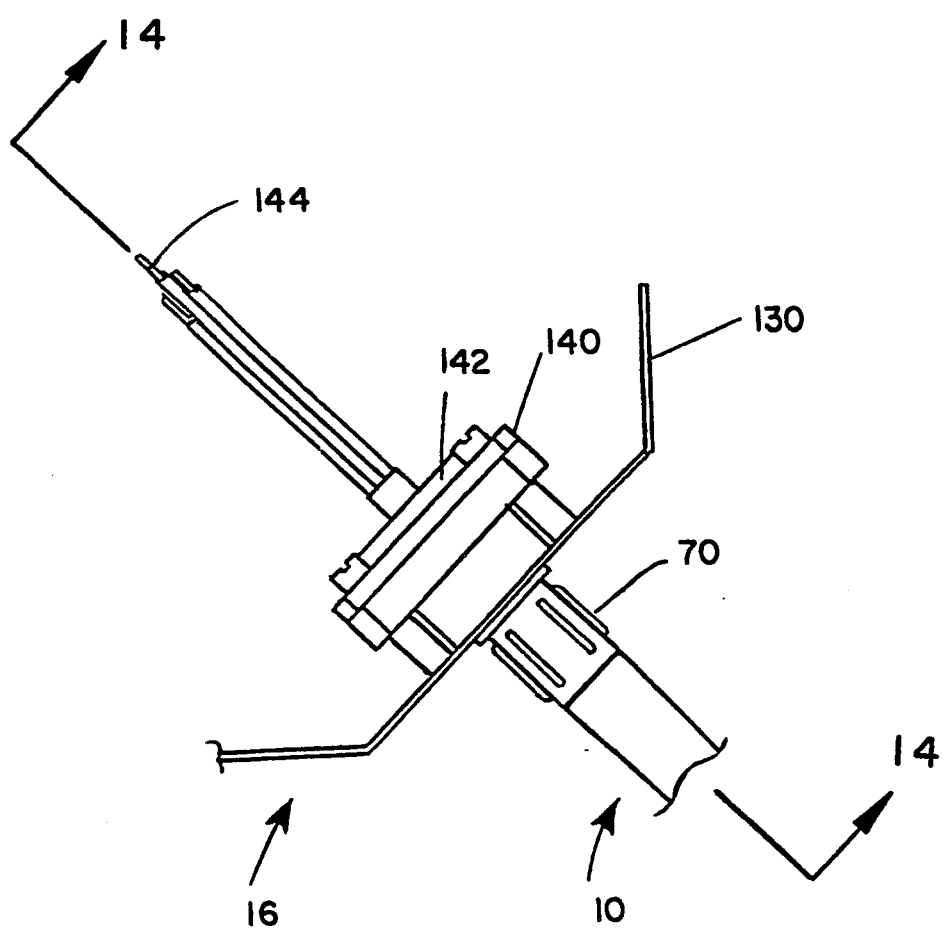
FIG. 12 is a side elevational view, broken away, of said probe in its relation to its control box.
Figure 13:
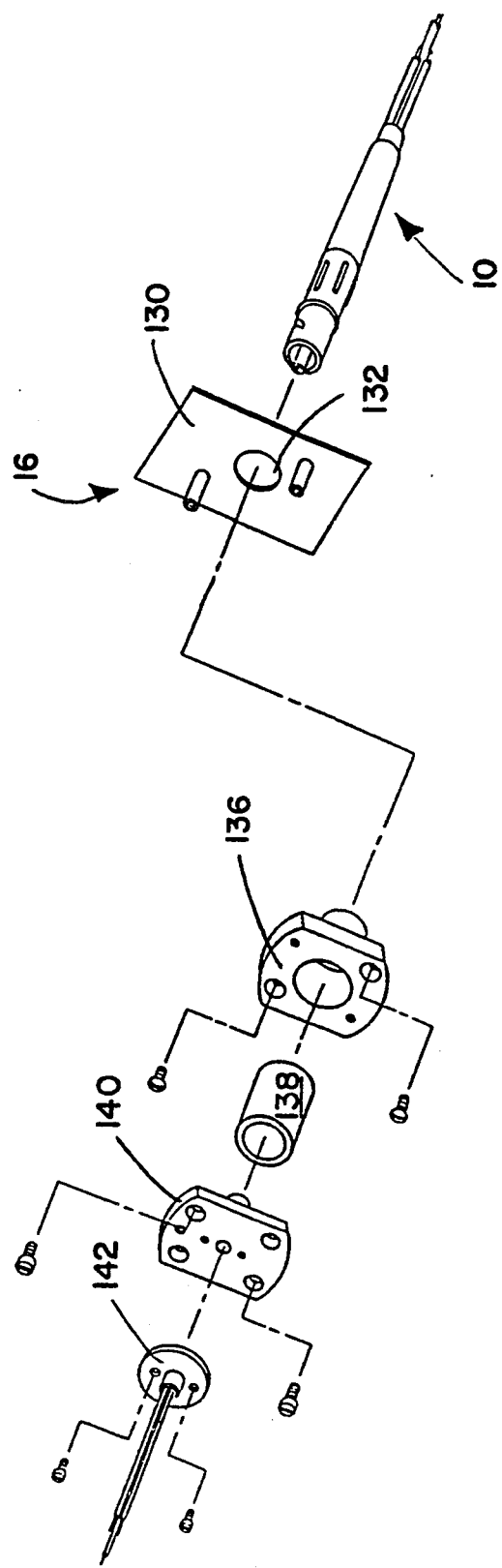
FIG. 13 is an exploded view, partially broken away, of what is shown in FIG. 12.
Figure 14:
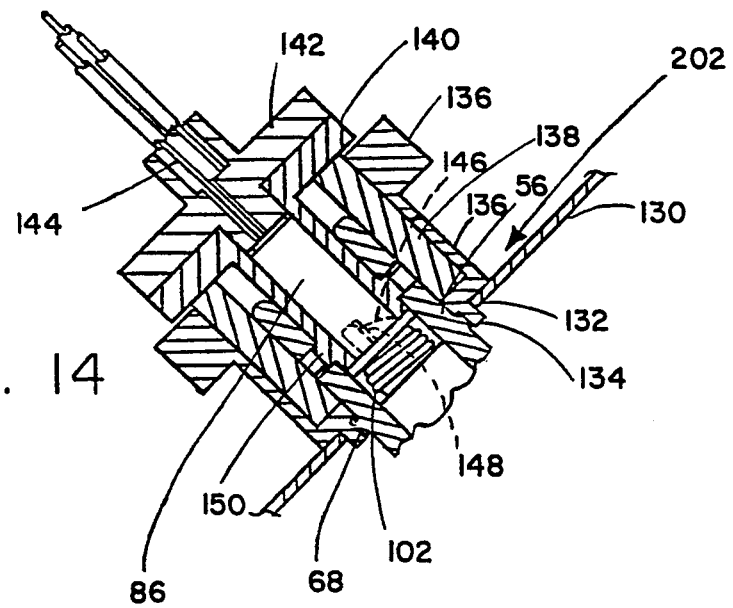
FIG. 14 is a sectional view of the subject matter of FIG. 12, taken at 14—14 thereof.

One end of probe 66 is thus mounted in control box 16, as more particularly shown in FIGS. 12 through 14.

There is shown a portion of wall 130 of control box 16. Extending through hole 132 therein is annulus tip 134 of bushing housing 136, in which is located elastomeric bushing 138 held in place by cast aluminum bayonet receptor 140, in which is secured fiber housing 142, through which extend optical fibers 144, which are potted in housing 142, with their ends polished in a common plane perpendicular to the axis of receptor 140.

Receptor 140 includes ramps and notches and ears configured exactly as described above and shown in FIG. 4 (40, 46; 42, 48; 50), except that in receptor 140 ears, ramps, and notches are all in that one part (ramps 146, notches 148, ears 150).

Within control box 16 is subassembly 150, which includes knurled nut 152 rotatable relative to steel follower 154 in which is secured an insulated optical fiber (not shown); nut 152 is turned so that the polished end of optical fiber 156 (the ESKA fiber above specified) is longitudinally forced against the polished tip of wishbone fiber optic coupler 158, of molded styrene acrylic copolymer, sold by Polysar Inc. under the number NAS 3071.

The single end of the wishbone is supported in a groove (not shown) in support 160, to align it with fiber 156. Each of the double ends 162 of the wishbone are supported in grooves (not shown) in support 160, which aligns them respectively with infrared LED light source 164 and spherical lens 166 optically connected to red LED light source 168. Insulating spacers 170 insulate from LED's 164 and 168 springs 172 and 174, which provide abutting forces between, respectively, wishbone legs and LED 164 and lens 166.

In aperture 176 in support 160 is mounted (not shown) a light sensor for detecting light lost from wishbone 158. Slider 178 resting on a depression in support 160 enables change in the amount of energy reaching the light sensor.

Figure 16:
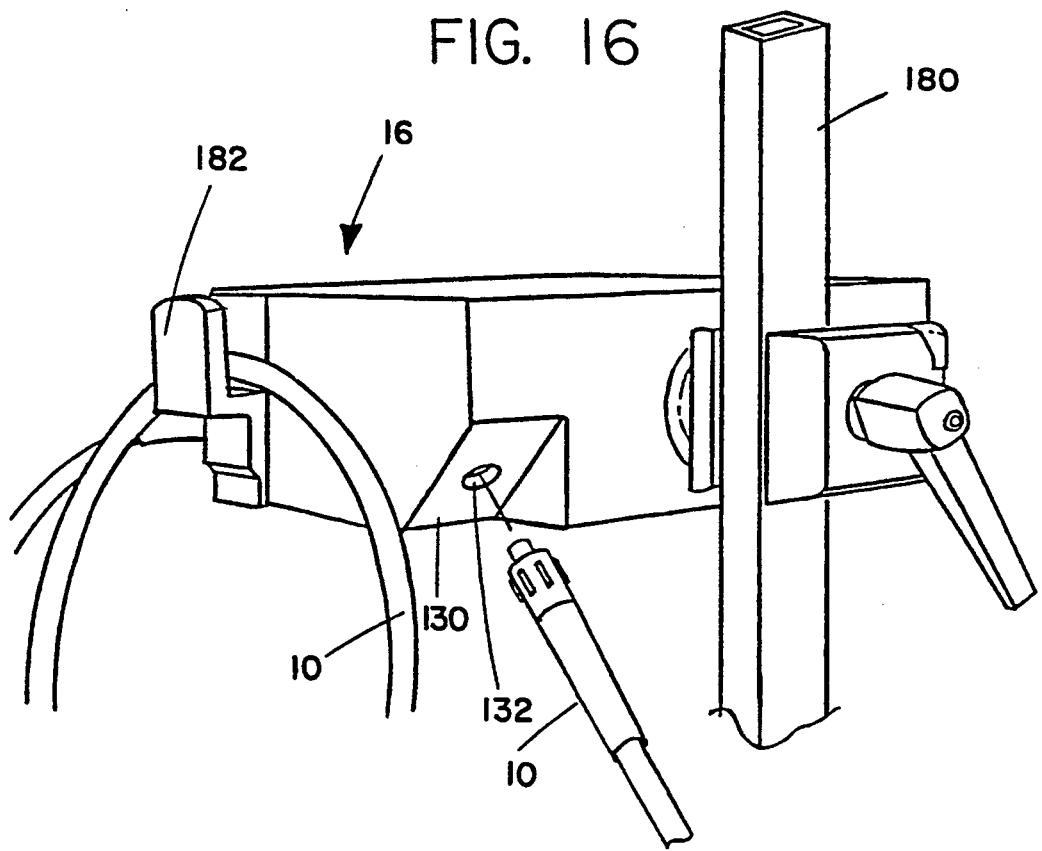
FIG. 16 is an isometric view, partially broken away, of a portion of said preferred embodiment.

In FIG. 16 box 16 is shown clamped onto post 180.

Figure 17:
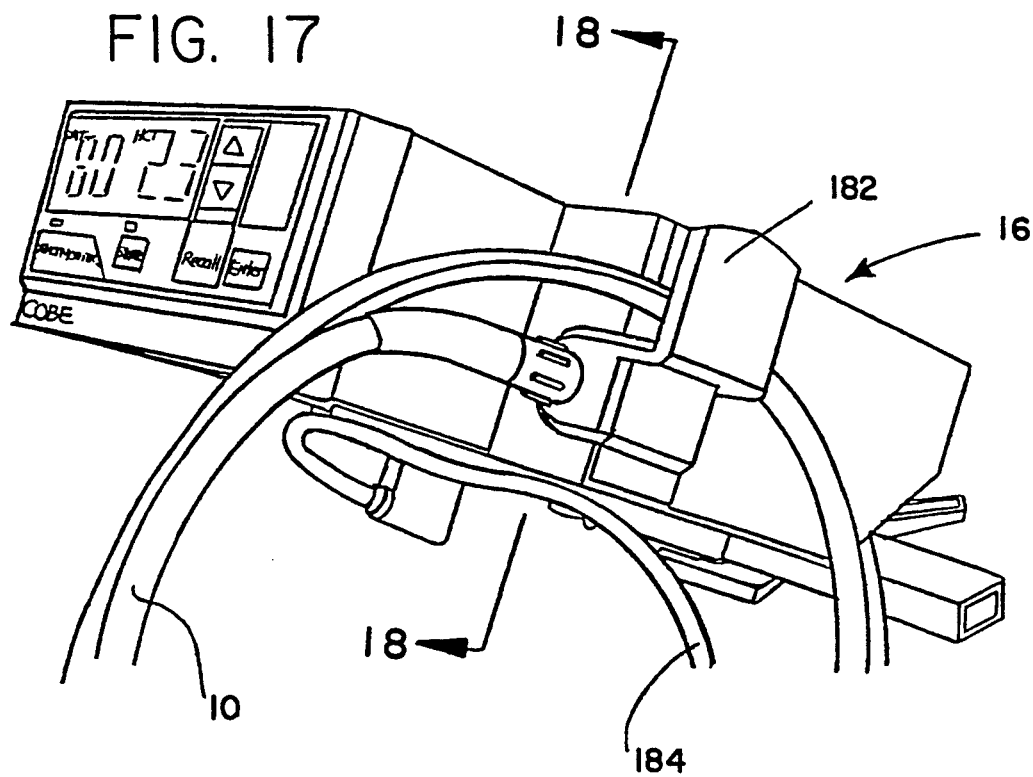
FIG. 17 is an isometric view, partially broken away, of a portion of said preferred embodiment.

Box 16 carries probe holder 182 and power cord 184 (FIG. 17; which also shows the probe end in the standardization port 190).

Figure 18:
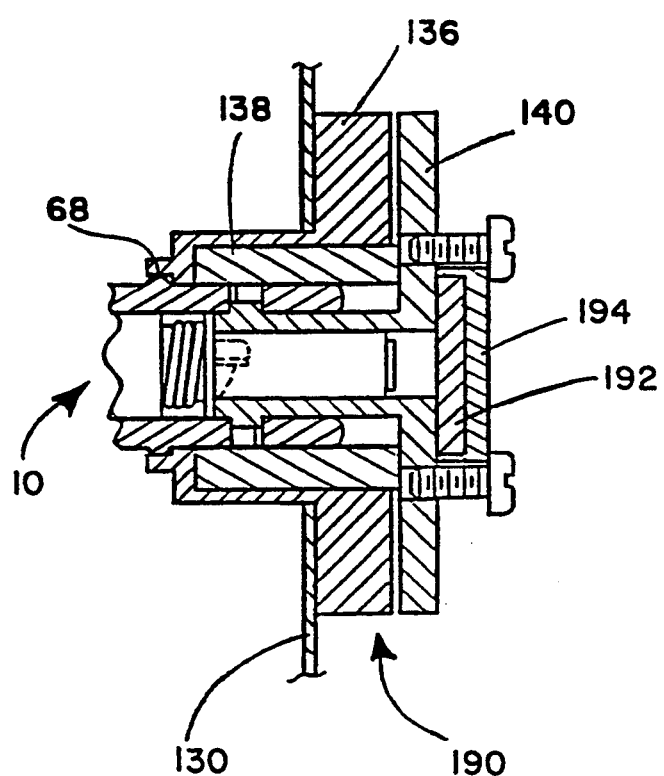
FIG. 18 is a sectional view taken at 18—18 of FIG. 17.

The standardization port 190 is shown in FIG. 18. Construction here is using the same elements shown in FIG. 14, except fiber optic housing 142 is omitted, and replaced by a photographer's gray card 192 characterized by known reflectivity at the IR and red wavelengths of the LED's above mentioned. Cover 194 holds card 192 in position.

OPERATION

In operation, to measure both hematocrit and oxygen saturation of blood, in each new use, with one end in operating port 202 (FIG. 14), the other end of probe 10 is introduced into standardization port 190 (FIG. 18) for inspection (for probes can be defective, as through fiber damage) and standardization (for even the same probe may change in its operating characteristics).

To inspect, voltage outputs are measured at both the near fiber and far fiber (infra) for both red and IR, and for each at both top intensity LED output and zero intensity LED output. The resultant information tells whether the probe is defective.

Next, a photosensor output voltage of the red LED is adjusted to 5 volts, as measured by a second, receiver photosensor (not shown) for the near fiber, in control box 16.

Figure 9:
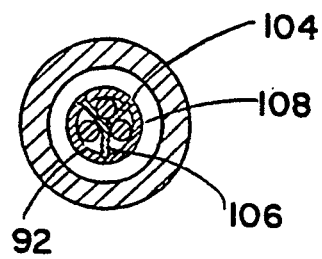
FIG. 9 is a sectional view taken at 9—9 of FIG. 8.
Figure 10:
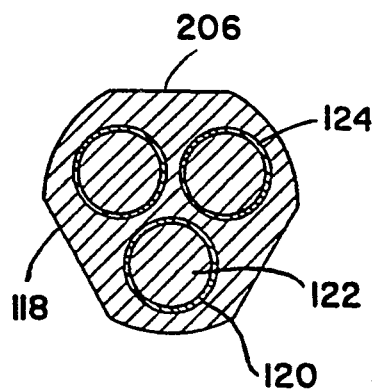
FIG. 10 is a sectional view taken at 10—10 of FIG. 8.
Figure 11:
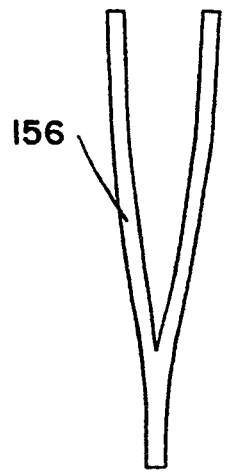
FIG. 11 is a plan view of a fiber optic element of the invention.

(Although FIG. 9 is somewhat diagrammatic, each fiber 108 is not equidistant from each of the others. In fact, the centerlines of the three fibers, cut by a perpendicular plane, define not an equilateral triangle, but rather a triangle in which the sides have lengths of 0.080 inches, 0.050 inches, and 0.050 inches; a source fiber is at one end of the 0.080 inch side; the fiber 0.050 inches from the source fiber is, of the two receiving fibers the one near the source fiber, and so is the "near fiber"; and the third fiber is the "far fiber".)

If this voltage cannot be reached, the probe is defective.

The ratio of red voltage output to IR voltage output is then adjusted to 1.15, to standardize.

The end of probe 66 in standardization port 190 is then withdrawn and introduced into side arm 52 (FIG. 5). Blood is made to flow through conduit 200 (FIG. 4).

Figure 15:
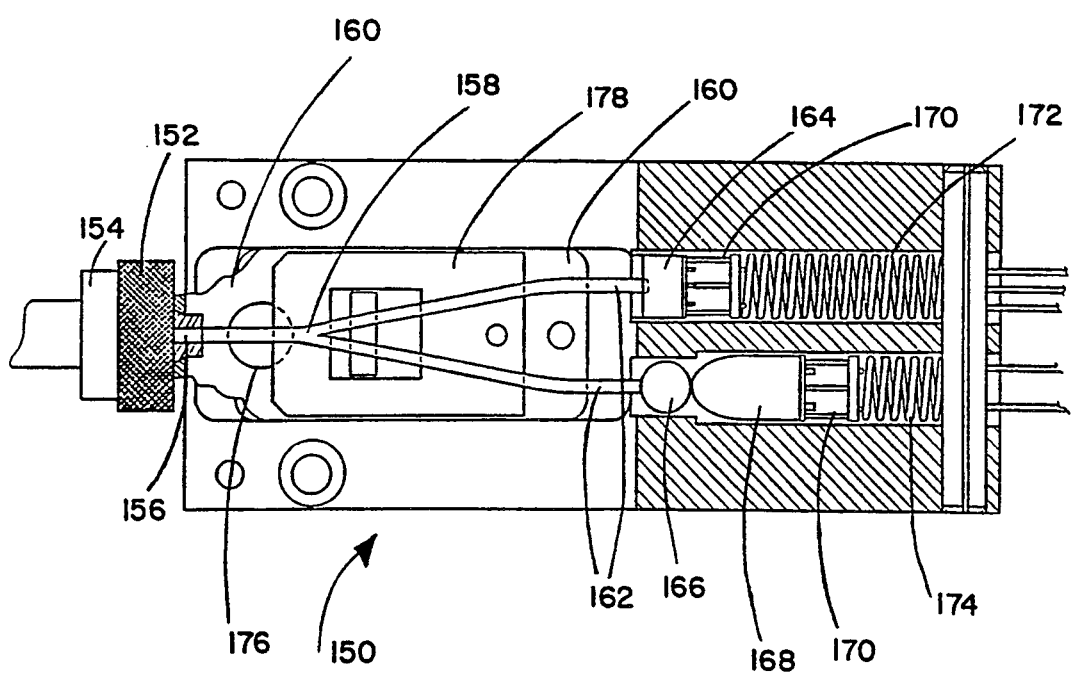
FIG. 15 is a view, partially in section, of a subassembly within said control box.

Red and IR light are then alternately pulsed from LED 168, fiber optic 162, and fiber optic 158; and from LED 164, fiber optic 162, and fiber optic 158. Fiber optic 158 has a polished end surface which is abuttingly pressed against the polished end of source fiber optic 108 (not shown in FIG. 15, but within cable 154), which extends on into tip 86 and against window 32.

Light passes in each pulse through the window and then through the flowing blood and out the near fiber 108 and far fiber 108, whence the light energy returns respectively through an abutted polished-end optical fiber in box 16 (not shown) and abutting near fiber 108, for voltage measurement by the near fiber photosensor (not shown) and through an abutted polished-end third optical fiber (not shown) in box 16, for voltage measurement by a far fiber photosensor (not shown).

The correct value of saturation is then displayed (FIG. 17), based on response from near fiber only of both IR and red, using automated known relationships.

At the same time, a value of hematocrit (based on ratio of IR responses from near fiber and far fiber) is displayed. That number must be calibrated (owing to patient variation) by testing a blood sample and adjusting the readout (FIG. 17) by any difference between it and the actual laboratory analysis.

We turn now to the operation, above mentioned, of introducing the end of probe 66 into side arm 52.

As collar 56 of probe 66 moves toward side arm 52 (FIG. 5), tip 86 moves into blind hole 36; during this movement ears 50 enter grooves 58 and shortly thereafter key 94 on tip 86 engages the upper portion of a ramp 40. Ears 50 then engage cam slot 60, and collar 56 is then rotated by hand to drive the collar toward pins 50, at the same time rotating key 94 and driving it down a ramp 40. As ears 50 reach the V in which ramp 62 terminates, key 94 drops into notch 48, which prevents further rotation of tip 86 (which would adversely cause scrubbing between the surfaces of window 32 and the polished end of probe tip 86, and would adversely affect correct orientation of optical fibers in the probe relative to the direction of blood flow). Hand rotation of collar 56 is then continued, to move cam portion 64 relative to ears 50 slightly away therefrom, decreasing spring force, but preventing ears 50 from going on their own back along track 62. Only one of ramps 40 participates at any one time; presence of two ramps permits choice of which is to be used, which gives greater flexibility in location of the probe relative to the ears. A white line extending axially on the outer surface locates where a groove 58 is; the ramp in use depends on the ear aligned with this white line.

Spring 102 presses the polished end 204 of tip 86 against smooth window 32 (FIG. 4); leaving air gapping is of course degrading to light conduction between end 204 fiber surfaces and the window.

Ribs 68 facilitate axially moving the ends of probe 66 into or out of cooperating receptacles as described. Ribs 70 facilitate rotating those ends, in both rotational directions.

Each end of probe 66 interacts in exactly the same way with ports 202 (FIG. 14) and 190 (FIG. 18), both ends being interchangeable for each place.

Bushing 138 may be axially compressed, in the embodiments of FIGS. 14 and 18, by tightening screws to bring bushing housing 136 and receptor 140 axially closer together, to impose additional friction on a probe tip 86 end therein to decrease likelihood of accidental removal. Further compression occurs when the entering probe collar is rotated. Bushing 138 also keeps the fibers in alignment, causing tip 86 and housing 142 to move together.

Circumferential projection 68 (not shown but present in FIG. 4) provides in FIG. 14 a stop causing members 140 and 142 to float toward the probe in rotation of the latter.

OTHER EMBODIMENTS

Other embodiments will occur to those skilled in the art.

Thus, the receptor assembly for optically connecting a probe to a conduit may be part not only of an oxygenator, but of other medical equipment instead, including a simple in-line transport (e.g., with nothing but two barbs on a conduit from which emerges a receptor for the probe of the invention, as the oxygenator above described has such a receptor in its side arm 210 and window 32) for interposition in line with, for example, an oxygenator.

What is claimed is:

1. Medical equipment for connection to a fiber optic probe which comprises
    a fluid conduit with an internal flat surface,
    a side arm connected sealedly with said conduit,
       a blind hole in said side arm,
           said blind hole including a hole flat surface parallel with said internal flat surface and defining therewith a light transmissive wall, and a projection protruding from said side arm.

2. An oxygenator which comprises
    a fluid conduit with an internal flat surface,
    a side arm connected sealedly with said conduit, a blind hole in said side arm,
said blind hole including a hole flat surface parallel with said internal flat surface and defining therewith a light transmissive wall, and a projection protruding from said side arm.

3. The oxygenator of claim 2 in which two ears are circumferentially spaced 180° and protrude perpendicularly from said side arm.

4. The oxygenator of claim 3 which includes a ramp descending in height in a conduit direction into a notch also extending in a said conduit direction.

5. A probe including at least one end, each said end comprising
a probe tip with a smooth face in which lie the extremities of three optical fibers and
an axially extending key adapted to ride on a ramp to, and mate with, a notch to prevent relative rotation between said tip and a side arm and maintain fiber optic orientation relative to said side arm,
said three optical fibers,
a collar, said collar including
a pair of camming slots circumferentially spaced 180° for cooperation with ears on said side arm, each of said slots including
a first portion angularly related to the axis of said collar to on rotation in a first direction drive said ears toward said collar and
a second portion angularly related to said axis to on said rotation drive said ears away from said collar,
a pair of longitundinally extending grooves for cooperation with said ears to allow their movement into said slots, and
spring support means, and
spring means biasing said tip away from said collar.

6. A probe as defined in claim 5 which includes two ends, each of said ends being a said end.

7. The combination of claim 5 in which said first portion is at an angle of 60° to said axis and has a circumferential length of 90° and said second portion is at an angle of 75° to said axis and has a circumferential length of 15°.

8. A receptor for the probe of claim 5 which includes an elastomeric bushing arranged to accept said probe collar.

9. A control box with an operating port configured to cooperate with said probe tip as in claim 5 against a surface including said optical fibers,
first optical light generating means optically connected to a first of said optical fibers, and
second optical light generating means optically connected to a second of said optical fibers.

10. The control box of claim 9 in which said first of said optical fibers is joined to said second of said optical fibers and both are joined in molded juncture to a third optical fiber said fibers being of integrally molded plastic.

11. The control box of claim 10 in which said juncture is in the configuration of a Y.

12. The control box of claim 9 which includes a testing port configured to cooperate with the probe of claim 4 to move and position said probe tip as in claim 5 spaced from a reflective surface.

13. The control box of claim 9 which includes an aperture for receiving light from an optical fiber, and adjustable aperture opening size means.

14. A fiber optic probe for connection to medical equipment, said medical equipment having a receptor for said probe, a hole in said receptor, said hole having a first end and second open end for entry of the probe into the hole, two ears that are circumferentially spaced 180° about said receptor and that protrude perpendicularly from said receptor and a ramp descending in height in a direction from the second end toward the first end into a notch also extending the direction from the second end toward the first end, said probe comprising:
at least one optical fiber, each optical fiber having an extremity,
a probe tip with a face in which lies the extremity of the each optical fibers,
an axially extending key adapted to ride on a ramp to, and mate with, a notch to prevent relative rotation between said probe tip and receptor and maintain fiber optic orientation relative to said receptor arm, and
a collar having an axis, said collar comprising,
a pair of camming slots circumferentially spaced 180° located to cooperate with said ears, each of said slots including,
a first portion at a first predetermined angular relation to the axis of said collar, the angular relation being predetermined to drive said ears toward said collar upon rotation in a first direction about the axis, and
a second portion at a second predetermined angular relation to the axis of said collar, the angular relation being predetermined to drive said ears away from said collar upon rotation in the first direction,
a pair of longitudinally extending grooves located to cooperate with said ears to allow their movement into said slots, and
spring support means, and
a spring means biasing said tip away from said collar.

15. The probe of claim 14 wherein the probe has a first end and a second end, each optical fiber has a first extremity and a second extremity, and wherein:
the first end has a corresponding probe tip with a face in which lies the first extremity of the each optical fiber,
the second end has a corresponding probe tip with a face in which lies the second extremity of each optical fiber, and
each one of the first and the second ends has an associated axially extending key, an associated collar, and an associated spring means biasing the corresponding tip away from the associated collar.

16. The probe of claim 14 in which said first portion of each camming slot is at an angle of 60° to said axis and has a circumferential length of 90° and said second portion of each camming slot is at an angle of 75° to said axis and has a circumferential length of 15°.

17. The probe of claim 14 which includes an elastomeric bushing arranged to accept said probe collar.

18. A control box for use with a fiber optic probe comprising:
an operating port,
a hole in said operating port said hole having a first end and second open end for entry of the probe into the hole, and
a projection protruding from said operating port,
a first optical fiber,
a first optical light generating means optically connected to the first optical fiber,
a second optical fiber, and a second optical light generating means optically connected to the second optical fiber, said first optical fiber extending from said first optical light toward said hole and said projection in said operating port, and said second optical fiber extending from said second optical light toward said hole and said projection in said operating port, wherein the operating port further comprises two ears that are circumferentially spaced 180° about a side arm and that protrude perpendicularly from said side arm, and a ramp descending in height in a direction from the second end toward the first end into a notch also extending in the direction from the second end toward the first end wherein the probe further comprises at least one optical fiber, each optical fiber having an extremity, a probe tip with a face in which lies the extremity of each optical fiber, an axially extending key adapted to ride on said ramp to, and mate with, said notch to prevent relative rotation between said probe tip and operating port and maintain fiber optic orientation relative to said operating port, and a collar having an axis, said collar comprising, a pair of camming slots circumferentially spaced 180° located to cooperate with said ears, each of said slots including, a first portion at a first predetermined angular relation to the axis of said collar, the angular relation being predetermined to drive said ears toward said collar upon rotation in a first direction about the axis, and a second portion at a second predetermined angular relation to the axis of said collar, the angular relation being predetermined to drive said ears away from said collar upon rotation in the first direction, a pair of longitudinally extending grooves located to cooperate with said ears to allow their movement into said slots, and spring support means, and a spring means biasing said tip away from said collar.

19. The control box of claim 18 in which said first portion of each camming slot is at an angle of 60° to said axis and has a circumferential length of 90° and said second portion of each camming slot is at an angle of 75° to said axis and has a circumferential length of 15°.

20. The control box of claim 18 in which said ears and said ramps are integral to a single part of the operating port and said ramps are on a single part of the operating port only.

21. The control box of claim 18 which includes an elastomeric bushing arranged to accept said probe collar.

22. The control box of claim 18 wherein the control box further comprises a testing port means to cooperate with the probe to move and position said probe tip spaced from a reflective surface.

23. The control box of claim 18 wherein the control box further comprises an aperture for receiving light from an optical fiber, and adjustable aperture opening size means.

24. A fiber optic connector comprising:

a receptor comprising:

a hole in said receptor said hole having a first end and second open end for entry of the probe into the hole, two ears that are circumferentially spaced 180° about said receptor and that protrude perpendicularly from said receptor, and a ramp descending in height in a direction from the second end toward the first end into a notch also extending the direction from the second end toward the first end, and a probe mating with the receptor, said probe comprising at least one optical fiber, each optical fiber having an extremity, a probe tip with a face in which lies the extremity of the each optical fiber, an axially extending key adapted to ride on said ramp to, and mate with, said notch to prevent relative rotation between said probe tip and receptor and maintain fiber optic orientation relative to said receptor, and a collar having an axis, said collar comprising, a pair of camming slots circumferentially spaced 180° located to cooperate with said ears, each of said slots including, a first portion at a first predetermined angular relation to the axis of said collar, the angular relation being predetermined to drive said ears toward said collar upon rotation in a first direction about the axis, and a second portion at a second predetermined angular relation to the axis of said collar, the angular relation being predetermined to drive said ears away from said collar upon rotation in the first direction, a pair of longitudinally extending grooves located to cooperate with said ears to allow their movement into said slots, and spring support means, and a spring means biasing said tip away from said collar.

25. The connector of claim 24 wherein the probe has a first end and a second end, each optical fiber has a first extremity and a second extremity, and wherein:

the first end has a corresponding probe tip with a face in which lies the first extremity of each optical fiber, the second end has a corresponding probe tip with a face in which lies the second extremity of each optical fiber, and each one of the first and the second ends has an associated axially extending key, an associated collar, and an associated spring means biasing the corresponding tip away from the associated collar.

26. The connector of claim 24 in which said first portion of each camming slot is at an angle of 60° to said axis and has a circumferential length of 90° and said second portion of each camming slot is at an angle of 75° to said axis and has a circumferential length of 15°.

27. The connector of claim 24 which includes an elastomeric bushing arranged to accept said probe collar.

28. An oxygenator for connection to a fiber optic probe, comprising an oxygenator housing, a fluid conduit with an internal flat surface, the conduit in fluid communication with the housing, a side arm connected sealedly with said conduit, a blind hole including a hole flat surface parallel with said internal flat surface and defining therewith a light transmissive wall, and a projection protruding from said side arm.

* * * * *